United States Patent
Roberts

(10) Patent No.: US 6,365,113 B1
(45) Date of Patent: *Apr. 2, 2002

(54) TRASH RECEPTACLE STERILIZATION METHOD AND APPARATUS

(76) Inventor: Jon L. Roberts, 529 Clear Spring Rd., Great Falls, VA (US) 22066

( * ) Notice: Subject to any disclaimer, the term of this patent is extended or adjusted under 35 U.S.C. 154(b) by 0 days.

This patent is subject to a terminal disclaimer.

(21) Appl. No.: 09/528,874

(22) Filed: Mar. 20, 2000

Related U.S. Application Data

(63) Continuation-in-part of application No. 09/014,559, filed on Jan. 28, 1998, now Pat. No. 6,039,928.

(51) Int. Cl.[7] .................................................. B01J 19/12
(52) U.S. Cl. .................................................... 422/186.3
(58) Field of Search ....................................... 422/186.3

(56) References Cited

U.S. PATENT DOCUMENTS

| | | | |
|---|---|---|---|
| 3,954,407 A | * | 5/1976 | Andary et al. ................ 21/83 |
| 4,088,445 A | * | 5/1978 | Ellis ............................... 21/83 |
| 4,100,415 A | * | 7/1978 | Blaisdell et al. ............. 250/455 |
| 4,625,119 A | * | 11/1986 | Murdock, III ........... 250/455.1 |
| 4,694,180 A | * | 9/1987 | Salisbury et al. ........ 250/455.1 |
| 4,772,795 A | * | 9/1988 | Sakurai et al. ........... 250/455.1 |
| 4,803,364 A | * | 2/1989 | Ritter ....................... 250/455.1 |
| 4,806,770 A | * | 2/1989 | Hylton et al. ............ 250/455.1 |
| 4,888,487 A | * | 12/1989 | Ritter ....................... 250/455.1 |
| 4,906,851 A | * | 3/1990 | Beasley .................... 250/455.1 |
| 4,973,847 A | * | 11/1990 | Lackey et al. ............ 250/445.1 |
| 5,126,572 A | * | 6/1992 | Chu ......................... 250/455.11 |
| 5,127,521 A | * | 7/1992 | Bourgue ..................... 206/362.1 |
| 5,487,877 A | * | 1/1996 | Choi ............................. 422/300 |
| 5,547,635 A | * | 8/1996 | Duthie, Jr. ..................... 422/24 |

FOREIGN PATENT DOCUMENTS

| | | |
|---|---|---|
| EP | 0493372 A2 | 4/1989 |
| WO | 99/26668 | 6/1999 |
| WO | 99/38540 | 8/1999 |
| WO | 00/06209 | 2/2000 |

* cited by examiner

*Primary Examiner*—Kathryn Gorgos
*Assistant Examiner*—Thomas H Parsons
(74) *Attorney, Agent, or Firm*—Roberts, Abokhair & Mardula, LLC

(57) ABSTRACT

A trash receptacle sterilization apparatus having ultraviolet sterilization in an enclosed container to kill bacteria and other disease carrying organisms. The receptacle has a vertical container into which a user places trash, other trash receptacles or other objects to be sterilized. An ultraviolet source within the container irradiates the trash receptacle thereby killing any microorganisms that might reside on or in the trash receptacles. Ultraviolet radiation below 200 nm can also be used thereby creating ozone gas having germicidal characteristics. The ozone gas is circulating in and around the trash receptacles thereby providing further sterilization together with the ultraviolet radiation. An interlocking switch turns the UV source off when the container is opened.

23 Claims, 2 Drawing Sheets

TRASH RECEPTACLE STERILIZATION METHOD AND APPARATUS

CROSS REFERENCES OF RELATED APPLICATIONS

This application is a Continuation in Part of application Ser. No. 09/014,559, filed Jan. 28, 1998, now U.S. Pat. No. 6,039,928, from which priority is claimed.

BACKGROUND OF THE INVENTION

The present invention relates generally to sterilization devices. More particularly this invention relates to a device for sterilizing the interior of trash receptacles using ultraviolet radiation and ozone gas in a closed container.

DESCRIPTION OF THE RELATED ART

It has long been known that germs are spread by, among other things, hand-to-hand contact. Hence there's been much in the literature recently concerning the washing of hands in order to prevent the spreading of the common cold as well as other microbes. Further, it has long been known that toothbrushes can be a source of the spreading of germs as well. Recently, it has been discovered that bacteria continue to live on writing implements used by individuals. Further, it is well known that trash receptacles can also carry microbes and therefore can be a vector for the spread of disease.

There is much prior art for the sterilization of various objects. For example, hospitals use sterilization routinely for surgical instruments. Typically, such sterilization occurs both chemically as well as through high-pressure, high temperature steam sterilization. This results in generally sterile instruments for use in surgery. The difficulty, of course, is that such devices are expensive, cumbersome, and are therefore not practical for the widespread sterilization of more common devices.

The spread of germs via bathroom articles has been the subject of prior inventions. Many inventors have dealt with the issues associated with toothbrush sterilization. For example, U.S. Pat. No. 3,954,407 to Andary et al. discloses an automatic toothbrush sterilization comprising ultraviolet lamps. Similarly U.S. Pat. No. 4,088,445 to Ellis discloses a sterilization holder and night-light for toothbrushes. U.S. Pat. No. 4,888,487 to Ritter discloses a toothbrush sterilizer with automatic control. U.S. Pat. No. 4,772,795 to Sakurai et al. discloses an ultraviolet sterilizer for dental implements. U.S. Pat. No. 4,803,364 to Ritter discloses a toothbrush conditioner comprising an ultraviolet radiation source. U.S. Pat. No. 4,806,770 to Hylton et al. discloses another form of a toothbrush holder having an ultraviolet lamp mounted within the housing.

U.S. Pat. No. 4,906,851 to Beasley et al. discloses yet another form of an ultraviolet toothbrush sterilizer and holder. U.S. Pat. No. 4,973,847 to Lackey et al. discloses a toothbrush sanitation device having an ultraviolet light source and a removable lid. U.S. Pat. No. 5,023,460 to Foster, Jr. et al. discloses a toothbrush sanitizer having a centrally mounted ultraviolet bulb with cavities for receiving toothbrushes. U.S. Pat. No. 5,126,572 to Chu discloses a toothbrush holder also having an ultraviolet source. U.S. Pat. No. 5,127,521 to Bourgue discloses a toothbrush holder also having an ultraviolet light source. U.S. Pat. No. 5,487,877 to Choi discloses a rest room organizer having a sterilization apparatus using an ultraviolet light for sterilizing bathroom articles. U.S. Pat. No. 5,547,635 to Duthei, Jr. discloses a general sterilization method and apparatus wherein microorganisms are exposed to ultraviolet light. Thus, it can be seen that much work has been done with respect to the sterilization of bathroom articles. However, no attention has been paid to the sterilization of more common objects, specifically trash receptacles which are also known to carry disease-producing microbes.

It would therefore be desirable to have a convenient, commonly available, inexpensive, and easy to use sterilization method and apparatus for sterilizing trash receptacles thereby preventing the transmission of object-borne disease spreading microorganisms.

SUMMARY OF THE INVENTION

It is therefore an object to the present invention to sterilize commonly used trash receptacles such as those found in offices, bathrooms and kitchens.

It is a further object of the present invention to provide a trash receptacle sterilization apparatus that can be commonly available and easy to use.

It is a further object of the present invention to provide a sterilization apparatus using ultraviolet radiation as a means of sterilization.

It is a further object of the present invention to combine ultraviolet sterilization and ozone sterilization together to more completely sterilize trash receptacles.

It is a further objective of the present invention to provide a sterilization device for sterilizing trash receptacles safely and without exposing a user to ultraviolet sterilization radiation.

It is a further object of the present invention to provide a trash receptacles sterilization unit that operates on normal wall current or battery power.

These and other objects of the present invention will become apparent to those skilled in the art by review of the specification that follows.

The present invention is a convenience, compact, and easy to use trash receptacle sterilization unit. The present invention comprises generally an ultraviolet light source particularly in the 200 to 300 nm wavelength range. This range has long been known for its germicidal and sterilization effects achieved by direct radiation. It is also well-known that ultraviolet radiation below 200 nm can produce small quantities of ozone from oxygen in the atmosphere. Ozone, in sufficient concentrations, is known to have significant germicidal and sterilization effects. Further, ozone, as a gas, is able to reach certain places and crevices in trash receptacles where ultraviolet radiation might not reach, especially when a number of trash receptacles are being sterilized together, simultaneously.

The ultraviolet light source of the present invention is mounted within a housing such that the ultraviolet radiation can shine directly upon and reflect onto the interior of trash receptacles. Thus, the interior of the housing also can reflect ultraviolet radiation in directions such as to both directly and indirectly reach all parts of the trash receptacles to be sterilized.

The ultraviolet light source can be mounted in a number of configurations. For example, where the trash receptacle sterilization apparatus is disposed vertically, the ultraviolet lamp can be a ring type lamp at the top of the housing, a tubular ultraviolet lamp source that can stand vertically in the housing, a series of ultraviolet lamps that can be disposed around the perimeter of the housing thereby directing radiation inward to trash receptacles that are contained vertically or horizontally within the housing.

The wavelength range of the ultraviolet radiation of the present invention also causes a small amount of ozone to be generated. This ozone is released into the housing and together with the ultraviolet radiation provides a more complete sterilization of the trash receptacles.

The present invention also comprises the top or lid which is hingedly or removably attached in to the lower housing. This cover or lid prevents ultraviolet radiation from escaping the container thereby protecting any users or those who pass by the sterilization apparatus.

Integral to the housing and its cover, is an interlocking switch which is biased in the "off" position. When the cover is placed over the sterilization apparatus, the switch is engaged and the ultraviolet radiation light source is turned on. When the cover is removed, for example when a trash receptacle top is opened, the ultraviolet radiation is immediately turned off as soon as the top is opened or the lid is lifted.

A timer circuit for the ultraviolet light source is also part of present invention. The timing circuit is activated as soon as the cover or lid of the sterilization apparatus is closed and the interlocking switch is engaged. The timer allows the ultraviolet light source to remain on for a predetermined amount of time. This time is consistent with sterilization of trash contained within the apparatus of the present invention. When the amount of time has expired, the ultraviolet light source is turned off thereby saving both power as well as prolonging the life of the ultraviolet light source(s). In the event that the top or lid is lifted or opened, as in the placement of trash in the trash receptacles, the timer is reset and, upon closing of the lid, the sterilization time period begins again.

As an integral part of the sterilization, an indicator light is provided whereby, when sterilization is proceeding, the indicator light is lit. When sterilization is not occurring, as in the case when the lid is lifted or the sterilization lamp has burned out, the indicator light is not lit. In this case, it will be clear to the user that either maintenance on the device must occur or the lid is not properly engaged with the interlocking switch.

The present invention can operate both on normal current found in homes, businesses, and buildings of all types as well as on battery power. Where battery power is used, it is anticipated that rechargeable batteries will be present in the present invention such that sterilization can continue to take place for some period of time even during power failures.

BRIEF DESCRIPTION OF THE DRAWINGS

The present invention is now described by way of example with references to the accompanying drawings:

Referring to FIG. 1 the present invention is shown. The sterilization apparatus of the present invention comprises the upper lid 50 hingedly attached to a lower container. Ultraviolet lamps 12 and 14 are attached to the upper lid 50. It should be noted that the number of lamps depicted in FIG. 1 is not meant to be limiting. For example in certain embodiments it may be more appropriate to have more than two lamps in the upper lid and the lower container portion. Further while the lamps are shown as individual tube type lamps, alternative shapes are well within the state-of-the-art including U-shaped lamps, ring-shaped lamps individual bulb-type lamps, and indeed any other lamp that will emit the appropriate ultraviolet radiation necessary for the sterilization.

Figure 1:
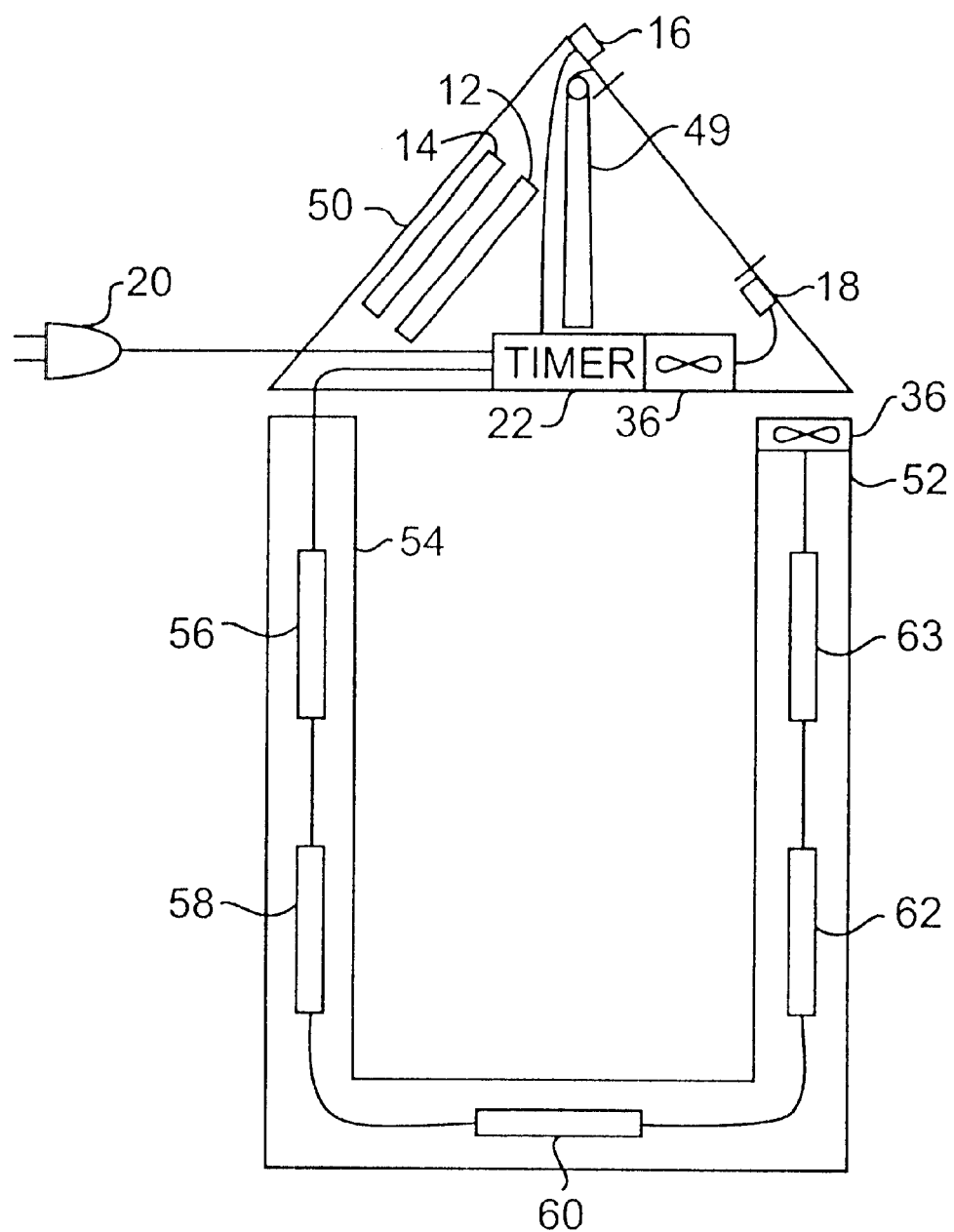
FIG. 1 shows a vertically disposed version of the present invention.

The sterilization apparatus receives power from the typical wall outlet via a plug 20 which is attached to an interlocking switch 18. This switch is biased in the "off" position so that when upper lid 50 in the open position all lamps 12, 14, 56, 58, 60, 62 and 63 are off. Conversely, when the door 49 to upper lid 50 is closed, switch 18 is closed and power is provided to lamps 12, 14, 56, 58, 60, 62 and 63. Further when all lamps are lit indicator light 16 is also lit showing anyone viewing the apparatus that ultraviolet radiation is being generated by the lamps contained in the apparatus. It should be noted that the position of indicator lights 16 is entirely arbitrary and can be placed anywhere on the apparatus to provide satisfactory convenient viewing by the user.

Trash is supported by the interior cylinder 54, which is of a transparent and/or porous material and functions as a supporting means. This supporting means 54 may be a screen or any other material that allows transmission of the ultraviolet radiation generated from lamps 56, 58, 60, 62 and 63. Further, supporting means 54 may also have circulation apertures in the supporting means to allow circulation of air within the sterilization apparatus.

As noted earlier, ultraviolet radiation in the 200 nm range generates ozone gas. In sufficient quantities, ozone gas can have a germicidal effect. Therefore, apertures in the supporting means 54 are provided to allow circulation of the ozone gas so that additional germicidal effects in addition to those of the ultraviolet radiation may occur. To further enhance circulation of air within the apparatus a small circulation fan 36 is provided. This fan is actuated when the interlocking switch 18 is actuated thereby providing power to the apparatus.

As part of the preferred embodiment, a timer circuit 22 is also provided. This timer circuit activates the ultraviolet sterilization lamps 12,14, 56, 58, 60, 62 and 63 as well as the recirculating fan 36 for a specific period of time. This period of time can be preset based upon the optimum time necessary to achieve sterilization. In the event that the door 49 to upper lid 50 is not opened within the time period established in the timer circuit 22, the sterilization lamps will go off after the passage of the optimum sterilization time. In event that the upper lid 50 is opened before the time for sterilization has expired, the timer 22 is reset and, when the door 49 to upper lid 50 is closed, the sterilization period begins again. In this fashion, power to the sterilization lamps is turned off after the appropriate sterilization period thereby saving lamp life and prolonging useful life of the ultraviolet sterilization lamps.

As noted above, inner cylinder 54 which comprises a material or any other material that is transparent to ultraviolet radiation is disposed inside an outer cylinder 52. Ultraviolet sterilization lamps 56, 58, 60, 62 and 63 are disposed between an inner cylinder and the outer cylinder. Light from the sterilization lamps is directed into the inner cylinder 54 in which trash may be placed. Upper lid 50 is removably attached to the lower cylinder 52.

It should be noted that the number of sterilization lamps depicted is arbitrary. More lamps could be used depending upon the configuration and size of the inner and outer cylinders. For example, a ring-shaped lamp could be disposed in the bottom of the cylinder and the upper lid thereby shining UV radiation both up and down the length of the trash receptacles to be sterilized. However, a sufficient number of lamps to achieve the sterilization desired must be used.

Again an interlocking switch 18 is actuated when an opening to upper lid 50 is opened over outer cylinder 52 thereby providing power to the sterilization lamps 56, 58, 60, 62 and 63. In addition, a circulation fan (not shown) is provided with the vertical embodiment to circulate any ozone produced by the sterilization lamps within the container. Power is provided to the vertical embodiment of FIG. 1 from conventional household power. A battery backup is also anticipated in event of power failure. In order to assistant in the circulation of ozone, inner cylinder 54 has apertures through the walls of the cylinder to allow for circulation of ozone gases produced by the sterilization lamps in and around the trash receptacles to be sterilized.

Figure 2:
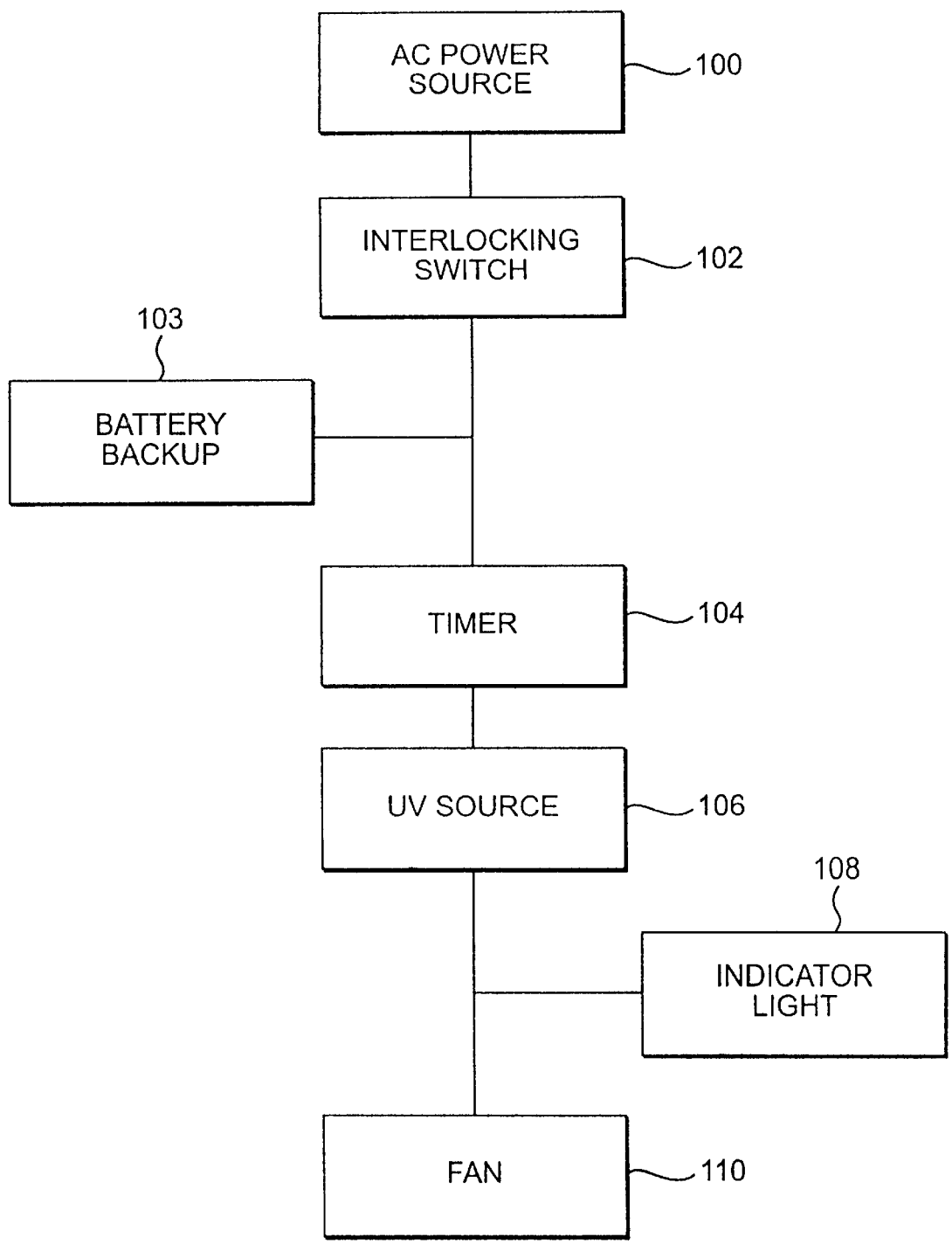
FIG. 2 is a simple schematic of the circuitry of the present invention.

Referring to FIG. 2, a simplified circuit diagram of the present invention is shown. Power from conventional household power 100 is provided to the sterilization unit. Power is provided directly to the interlocking switch 102 so that when the upper lids of the various embodiments are closed, power is provided to the entire device. A battery backup 103 is also provided such that power from the wall outlet also recharges the battery backup 103. Power then flows to the timer circuit 104 which is preset to an optimum sterilization time. When switch 102 is actuated and timer 104 begins, power is applied to the sterilization lamp(s) 106. As noted earlier it is anticipated that numerous configurations of sterilization lamps in size, physical shape, and number are anticipated as within the scope of the present invention.

A method and apparatus for sterilization of trash receptacles has been shown. Various alternative embodiments of the present invention are possible by utilizing alternate arrangements and geometries. Common to all of these embodiments are the sterilization lamps, means for supporting trash in such a fashion that ultraviolet radiation can reach the various trash receptacles to sterilize them, circulation means to circulate in any ozone produced by the ultraviolet lamps, and power and timing circuits to provide timed sterilization for trash receptacles that are stored in the sterilization apparatus of the present invention.

It will be appreciated by those skilled in the art that other embodiments may be possible employing the common elements of the present invention that has been disclosed.

What is claimed is:

1. A trash receptacle sterilization apparatus comprising:
   (A) a lower container;
   (B) an upper lid attached to the lower container;
   (C) a first ultraviolet radiation source disposed within the upper lid;
   (D) a trash receptacle holder for supporting trash receptacles disposed within the lower container;
   (E) a power supply connected to the ultraviolet radiation source; and
   (F) an interlocking switch connected between the power supply and the ultraviolet radiation source biased to the off position such that when the upper lid is in an open position the interlocking switch is not engaged and no power is supplied to the ultraviolet radiation source and when the upper lid is closed, the interlocking switch is engaged and power is supplied to the ultraviolet radiation source.

2. The trash receptacle sterilization apparatus of claim 1 wherein the first ultraviolet source emits ultraviolet radiation below 200 nm and creates ozone gas.

3. The trash receptacle sterilization apparatus of claim 2 wherein the first ultraviolet source comprises a plurality of ultraviolet emitting lamps.

4. The trash receptacle sterilization apparatus of claim 2 wherein the trash receptacle holder is transparent to the ultraviolet radiation.

5. The trash receptacle sterilization apparatus of claim 4 wherein the trash receptacle holder further comprises air circulation apertures for allowing the circulation of the ozone produced by the ultraviolet radiation.

6. The trash receptacle sterilization apparatus of claim 5 further comprising an air circulation fan for circulating ozone through the circulation apertures and throughout the lower container.

7. The trash receptacle sterilization apparatus of claim 1 wherein the first ultraviolet source emits ultraviolet radiation above 200 nm.

8. The trash receptacle sterilization apparatus of claim 7 wherein the ultraviolet source comprises a plurality of ultraviolet emitting lamps.

9. The trash receptacle sterilization apparatus of claim 7 wherein the trash receptacle holder is transparent to the ultraviolet radiation.

10. The trash receptacle sterilization apparatus of claim 1 wherein the lower container is oriented vertically to allow trash receptacles to be placed vertically therein for sterilization.

11. The trash receptacle sterilization apparatus of claim 1 wherein the lower container is oriented horizontally to allow trash receptacles to be placed horizontally therein for sterilization.

12. The trash receptacle sterilization apparatus of claim 1 wherein the first ultraviolet source comprises at least one ultraviolet emitting lamp.

13. The trash receptacle sterilization apparatus of claim 1 further comprising a second ultraviolet source disposed within the upper lid.

14. The trash receptacle sterilization apparatus of claim 13 wherein the interlocking switch further controls power to the second ultraviolet source.

15. The trash receptacle sterilization apparatus of claim 13 where the second ultraviolet source emits ultraviolet radiation below 200 nm.

16. The trash receptacle sterilization apparatus of claim 13 where the second ultraviolet source emits ultraviolet radiation above 200 nm.

17. The trash receptacle sterilization apparatus of claim 1 further comprising an indicator light connected to the interlocking switch and the first ultraviolet source such that the indicator light is lit only when the interlocking switch is engaged and the first ultraviolet source is illuminated.

18. The trash receptacle sterilization apparatus of claim 1 wherein the power supply further comprises a battery.

19. The trash receptacle sterilization apparatus of claim 18 wherein the battery is rechargeable and is recharged by the power supply.

20. A trash receptacle sterilization apparatus comprising:
   (A) a substantially vertically oriented lower container for placement of trash;
   (B) an upper lid attached to the substantially vertically oriented lower container;
   (C) a first substantially vertically oriented ultraviolet radiation source disposed within the lower container for sterilizing trash contained therein;
   (D) a substantially vertically oriented trash receptacle holder for supporting trash disposed within the lower container;
   (E) a power supply connected to the ultraviolet radiation source; and
   (F) an interlocking switch connected between the power supply and the first ultraviolet radiation source biased to the off position such that when the upper lid is in an open position the interlocking switch is not engaged and no power is supplied to the ultraviolet radiation source and when the upper lid is closed, the interlocking switch is engaged and power is supplied to the ultraviolet radiation source.

21. The trash receptacle sterilization apparatus of claim 20 wherein the ultraviolet radiation source emits ultraviolet radiation below 200 nm and creates ozone gas.

22. The trash receptacle sterilization apparatus of claim 21 wherein the ultraviolet radiation source emits ultraviolet radiation above 200 nm.

23. The trash receptacle sterilization apparatus of claim 21 further comprising a circulation fan for circulating the ozone gas throughout the lower container.

* * * * *